United States Patent
Newton, Jr.

(10) Patent No.: US 9,254,218 B2
(45) Date of Patent: Feb. 9, 2016

(54) EXTERNAL URINARY CATHETER SYSTEM

(71) Applicant: Milton A. Newton, Jr., Desert Hot Springs, CA (US)

(72) Inventor: Milton A. Newton, Jr., Desert Hot Springs, CA (US)

(*) Notice: Subject to any disclaimer, the term of this patent is extended or adjusted under 35 U.S.C. 154(b) by 0 days.

(21) Appl. No.: 13/827,185

(22) Filed: Mar. 14, 2013

(65) Prior Publication Data

US 2013/0338617 A1 Dec. 19, 2013

Related U.S. Application Data

(60) Provisional application No. 61/613,751, filed on Mar. 21, 2012.

(51) Int. Cl.
*A61F 5/44* (2006.01)
*A61F 5/453* (2006.01)
*A61F 5/451* (2006.01)

(52) U.S. Cl.
CPC ............ *A61F 5/453* (2013.01); *A61F 5/451* (2013.01)

(58) Field of Classification Search
CPC ......... A61F 5/445; A61F 5/448; A61F 5/449; A61F 5/451; A61F 5/453; A61F 4/00; A61F 5/4408; A61F 5/44
USPC .......................................... 604/349–351, 353
See application file for complete search history.

(56) References Cited

U.S. PATENT DOCUMENTS

| | | | | |
|---|---|---|---|---|
| 2,476,375 | A * | 7/1949 | Kent | 604/353 |
| 4,656,675 | A * | 4/1987 | Fajnsztajn | 4/144.4 |
| 4,846,816 | A * | 7/1989 | Manfredi | 604/323 |
| 4,846,909 | A * | 7/1989 | Klug et al. | 156/232 |
| 4,997,427 | A * | 3/1991 | Bowen | A61F 5/453 |
| | | | | 604/349 |
| 5,495,858 | A * | 3/1996 | Steer et al. | 128/885 |
| 5,897,540 | A * | 4/1999 | Grundke et al. | 604/352 |
| 6,010,489 | A * | 1/2000 | Blackburn | 604/353 |
| 6,117,120 | A * | 9/2000 | Heininger | 604/349 |
| 6,551,293 | B1 * | 4/2003 | Mitchell | 604/353 |
| 7,066,918 | B2 * | 6/2006 | Charles | 604/327 |
| 2002/0007160 | A1 * | 1/2002 | Miskie | 604/349 |
| 2009/0270822 | A1 * | 10/2009 | Medeiros | 604/347 |
| 2011/0016606 | A1 * | 1/2011 | Bothwell | 2/114 |
| 2011/0270203 | A1 * | 11/2011 | Sharpe et al. | 604/326 |
| 2012/0238976 | A1 * | 9/2012 | Foster | 604/353 |
| 2012/0316522 | A1 * | 12/2012 | Carter et al. | 604/353 |

* cited by examiner

*Primary Examiner* — Philip R Wiest
*Assistant Examiner* — Ariana Zimbouski
(74) *Attorney, Agent, or Firm* — Christie, Parker & Hale, LLP

(57) ABSTRACT

A male external urinary catheter system includes an external collector having a proximal portion configured to receive a user's penis and a distal portion, a retaining structure configured to urge the proximal end of the external collector against the user's body adjacent the base of the penis, and a drainage container coupled to the distal portion of the external collector.

10 Claims, 6 Drawing Sheets

EXTERNAL URINARY CATHETER SYSTEM

CROSS-REFERENCE TO RELATED APPLICATION

This application claims priority to and the benefit of U.S. Provisional Application No. 61/613,751, filed Mar. 21, 2012, the entire contents of which are incorporated herein by reference.

FIELD

The present invention relates to an external urinary catheter system.

BACKGROUND

Urinary catheters may be used to treat or manage incontinence by allowing a patient's urine to drain freely from the bladder for collection. Traditional male urinary catheters include tubes placed within the urethra and condom type catheters. Each of these types of catheters has drawbacks. Temporary tubular catheters can cause significant discomfort due to frequent insertion, and long-term tubular catheters may lead to urinary tract infections. Condom type catheters also may lead to urinary tract infections. In addition, due to friction between the penis and the condom, as well as a result of adhesives, inflammation and irritation of the penis may occur. Some traditional urinary catheters also require the assistance of medical professionals.

SUMMARY

The present invention relates to external urinary catheter systems for men.

In embodiments of the invention, a male external urinary catheter system includes an external collector having a proximal portion configured to receive a user's penis and a distal portion, a retaining structure configured to urge the proximal end of the external collector against the user's body adjacent the base of the penis, and a drainage container coupled to the distal portion of the external collector.

The retaining structure may be configured to provide pressure to the user's body to impede urinary drainage from the user's penis. The retaining structure may be configured to provide pressure to the user's body to impede urinary drainage from the user's penis while the user is sitting or laying.

The retaining structure may be a strap connected to the external collector. The strap may be configured to wrap around the user's body. The strap may be configured to be affixed to the user's clothing.

The retaining structure may be a garment having at least one opening in the front, the at least one opening having an opening diameter, and the distal portion of the external collector may include a first portion having a first diameter and a second portion at the end of the distal portion having a second diameter that is smaller than the first diameter. The second portion may be smaller than the opening diameter and the first diameter may be larger than the opening diameter.

The distal portion of the external collector may include threads configured to mate with a threaded opening of the drainage container.

The distal portion of the external collector may include threads configured to mate with tubing that is coupled to the drainage container.

The drainage container may be a leg bag.

The drainage container may include a backflow prevention device at an opening of the drainage container.

The external collector may be substantially cylindrical.

The external collector may include an air vent at the proximal portion. The air vent may be air permeable and liquid impermeable.

The external collector may include a circumferential groove at the proximal portion.

A pressure pad may be disposed at the proximal portion and may be configured to bear against the user's body.

An internal cushion may be disposed inside the external collector. An external cushion may be disposed on an external surface of the external collector.

DETAILED DESCRIPTION

Figure 3A:
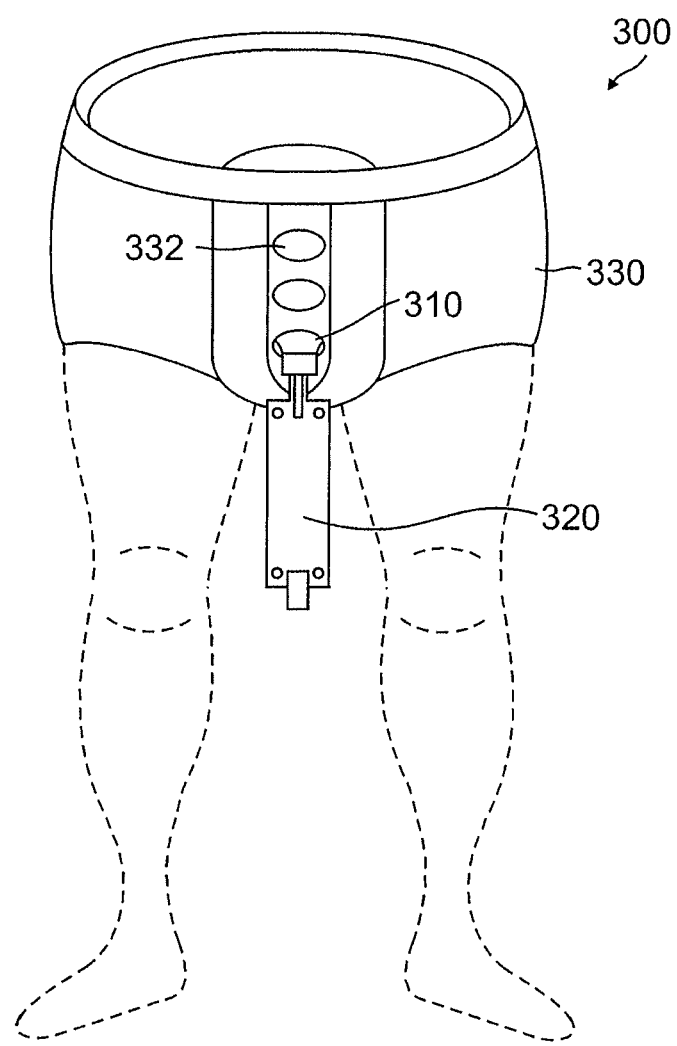
FIG. 3A is a schematic view of an external urinary catheter system according to an embodiment of the present invention.

As shown in FIG. 3A, a male external urinary catheter system 300 includes an external collector 310 having a proximal portion configured to receive a user's penis and a distal portion, a retaining structure 330 configured to urge the proximal end of the external collector against the user's body, and a drainage container 320 coupled to the distal portion of the external collector. When worn by a user, the catheter system may impede or substantially prevent urinary drainage from the penis while sitting or laying. While not being bound by any theory, it is believed that while sitting or laying, the system provides sufficient pressure against a user's urethra to impede or substantially cut off urine flow. However, when standing, pressure against the user's urethra is lessened, and urine flow can occur. Such a system alleviates many of the problems of traditional urinary catheters, as the system is not invasive, does not require the use of glues or other adhesives, and does not require the assistance of a medical professional. Accordingly, the system is an effective and comfortable solution for males suffering from urinary incontinence, as it allows mobility without the fear of leakage or embarrassment.

Figure 1A:
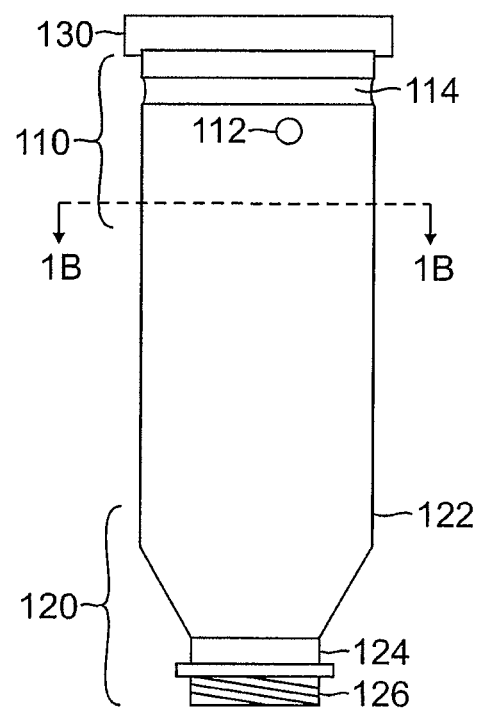
FIG. 1A is a schematic view of an external urinary collector according to an embodiment of the invention.

FIG. 1A depicts an external urinary collector 100 according to embodiments of the present invention. The external collector 100 includes a proximal portion 110 configured to receive a user's penis and a distal portion 120. The external collector may be any suitable sheath-like shape such as that of a tube. For example, the external collector may be prismatic (e.g., a square prism, a pentagonal prism, or the like) or cylindrical (e.g., a right circular cylinder, an elliptical cylinder, or the like). In one embodiment, the external collector is substantially cylindrical.

The external collector 100 may be made of any suitable material. For example, the collector may be made of any suitable type of plastic, plastic-like, or polymeric material. Preferably, the collector is made of a bacteria resistant material that may be easily cleaned. In some embodiments, the collector 100 is substantially transparent. The collector is a self-supporting structure, e.g., it is substantially semi-rigid or rigid, so that a force applied to the distal portion 120 of the collector 100 is transmitted to proximal portion 110. While the collector is substantially rigid, it may relatively thin so that it does not take up too much space, however, sufficiently thick that it is not susceptible to breakage and retains its rigidity under the forces encountered in its use.

The external collector 100 may be any suitable size, may be custom made for each user, or a plurality of different sizes may be manufactured so that they collector may be purchased to fit. For example, the external collector may have an external diameter of 1½ to 2½ inches or larger and a length (from end to end) of 4 to 6 inches or larger. In some embodiments, the external collector may have an external diameter of 2⅛ inches and a length of 5½ inches. However, these sizes are merely exemplary, and any suitable size may be used. The external collector should have a sufficiently large inner diameter to accept a user's penis comfortably (e.g., it should loosely receive the user's penis and allow space for changes in size while the user is wearing the device), but should not have an overly wide diameter so that it is relatively comfortable and applies pressure to a user's urethra. Furthermore, while the collector is shown as having a substantially constant cross sectional width with the exception of the distal end, the cross sectional width of the collector may vary. The external collector should have a sufficient length to comfortably fit the user's penis, and should allow additional room for changes in size while the user is wearing the device. However, if the external collector is too long, it may be uncomfortable to wear and it may also be unsightly.

The external collector may also include an air vent 112. The air vent 112 may be located at any suitable portion of the external collector. For example, the air vent 112 may be located at the proximal portion 110 of the external collector 100. The air vent may be a hole or opening in the external collector. Alternatively, the air vent may be a gas permeable, liquid impermeable valve. The vent aids in preventing the drainage container from becoming inflated with air. That is, when initially putting on the system, and also, through natural movements during the day, air may enter the external collector. If no vent is present, the drainage container may fill with air, which can be uncomfortable for the user or lead to leakage of urine from the container. When the air vent 112 is present at the proximal portion 110 of the external collector 100, the air filling phenomenon may be eliminated or reduced. Furthermore, even when the air vent is simply a hole, urine may not escape through the hole because of the vent's location in relation to the end of the user's penis. However, the air vent 112 can be located at any suitable portion of the collector and may be any suitable type of air vent that allows air to escape the system.

The external collector may optionally include a groove 114 around the circumference of the external collector. The groove 114 may be located near the proximal portion 110 of the external collector. The groove 114 is configured to receive a condom-like sleeve. For example, the condom-like sleeve may have two open ends, each end being similar to the open base of a condom. Each end may include a rib generally found at the open base of a condom. One end (i.e., a rib) of the condom-like sleeve may be seated securely in the groove 114. When the external collector is on the user's penis, the condom-like sleeve may be unrolled up the user's penis to seal the proximal end of the external collector 100. The sleeve may be rolled back down to the groove 114 when not needed. The sleeve may be used at all times, or, alternatively, the sleeve may be used only at night, when additional leakage protection is desired. The sleeve may be replaceable. While it is believed that the use of the sleeve is not necessary, as the system substantially prevents drainage while in a laying position, the use of a condom-like sleeve may be a comforting leakage back-up system for side and stomach sleepers.

The distal portion 120 of the external collector 100 includes a first portion 122 and a second portion 124. The second portion 124 is distal to the first portion 122 (i.e., it is closer to the end of the collector). The first portion 122 has a first diameter and the second portion 124 has a second diameter. The first diameter may be the diameter of the external collector. The second diameter is smaller than the first diameter. In other words, the external collector tapers to become smaller toward the end of the distal portion. In some embodiments, the first diameter may be about 2⅛ inches and the second diameter may be about 1 inch. The second diameter is sufficiently small to extend through an opening in underwear, while the first diameter is sufficiently large so that it does not extend through the opening, as will be described below. However, in some embodiments, when use with underwear is not desired, a tapered end is not necessary.

A connection member 126 is at the end of the distal portion 120. Any suitable type of connection member 126 may be used to couple the collector 100 to the drainage container, described below. For example, an interference fit or fastener may be used to couple the collector 100 to the drainage container. If an interference fit is used, a tube may be forced onto a connection member having, e.g., a slightly smaller diameter. However, preferably, a screw-top type fastener is used. Such a closure device may be made relatively inexpensively, is easy to use, and prevents leakage through the seal. For example, male threads may be present at the end of the distal portion 120. The male threads may be configured to couple to female threads at the opening of the drainage container, or alternatively, the male threads may be configured to be coupled to female threads in tubing that is coupled to the drainage container. However, in some embodiments, the threads may be reversed (e.g., female threads at the end of the distal portion and male threads at the opening of the drainage container or tubing).

The collector 100 may optionally include a pressure pad 130. The pressure pad is a donut-shaped cushion coupled to the end of the distal portion 110 and is configured to be adjacent to the user's body when the system is used. Because the system is used for extended periods of time, it can become uncomfortable to wear, as it is made of a rigid or semi-rigid plastic or polymeric material. Accordingly, a pressure pad 130 may be coupled to the collector to cushion the device. The pressure pad 130 may be made of a soft material, e.g., fabric, foam rubber, gel, or other suitably soft material. In some embodiments, the cushions may be made of a medical grade material, such as an anti-bacterial gel, latex, or silicone type material that may be washed so that the collector is hygienic. The pressure pad may be any suitable thickness, for instance 1/16 to ¼ inches. In some embodiments, the pressure pad may be ⅛ inch thick. The pressure pad 130 may be permanently affixed to the end of the distal portion 110, or alternatively, the pressure pad 130 may be removably coupled to the end of the distal portion 110.

Figure 1B:
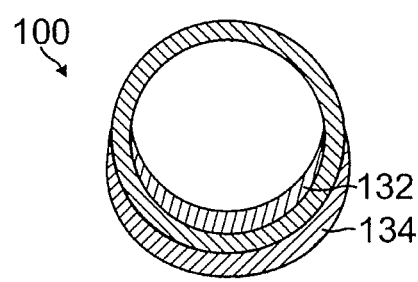
FIG. 1B is a cross-sectional view of the external urinary collector of FIG. 1A.

FIG. 1B depicts a cross-sectional view of the collector 100 of FIG. 1A. When the collector is used, it may irritate the user's penis and testicles. As such, as shown in FIG. 1B, the collector may optionally include an internal cushion 132 and external cushion 134. The internal cushion 132 may be located on a lower region of the collector when it is in use. Alternatively, the cushion 132 may be located around the entire internal surface of the collector so that the collector may be used in any orientation. The cushion 132 may substantially extend the length of the collector, or it may be any suitable length. For instance, if the collector is 6 inches, the cushion may extend 5½ inches. The external cushion 134 may be located on a lower region of the collector when it is in use. Alternatively, the cushion 134 may be located around the entire external surface of the collector so that the collector may be used in any orientation. The cushion 134 may extend a sufficient length so that it cushions the device against the user's testicles. In some embodiments, when the groove 114 is included, the cushion 134 may begin below the groove and may extend about 3 inches. However, the external cushion 134 may extend any suitable length. The internal and external cushions may be made of a soft, non-chafing material, e.g., fabric, foam rubber, gel, or other suitably soft material. In some embodiments, the cushions may be made of a medical grade material, such as an anti-bacterial gel, latex, or silicone type material that may be washed so that the collector is hygienic. The cushions may be any suitable thickness, for example ¹/₁₆ to ¼ inches thick. In some embodiments, the cushions are ⅛ inch thick. Each of the cushions may be permanently affixed to the collector, or alternatively, one or both of the cushions may be removably coupled to the collector.

Figure 2:
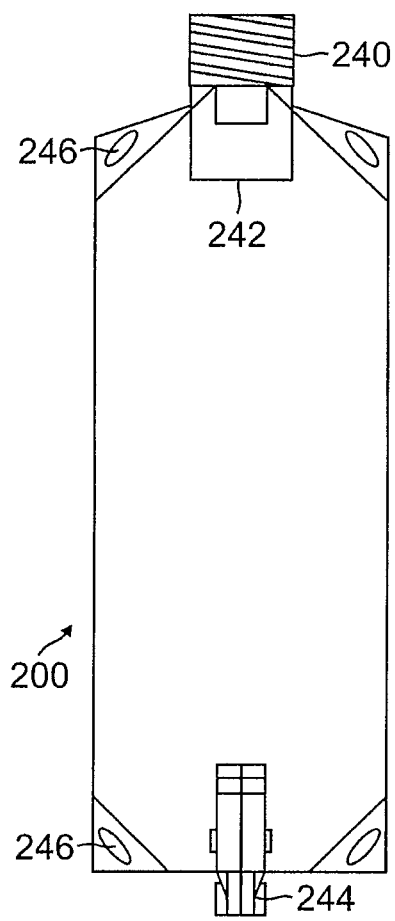
FIG. 2 is a schematic view of a drainage container according to an embodiment of the invention.

FIG. 2 depicts a drainage container 200 according to embodiments of the present invention. The drainage container 200 could be a drainage bag adapted to be strapped to a user's leg as shown in FIG. 2. Alternatively, the drainage container 200 could be any other suitable drainage container, such as a night bag or a solid jar drainage container. Drainage bags are typically stored substantially flat and then expand when filled. Drainage bags vary in size according to use. Any suitable size drainage bag may be used. For instance, in some embodiments, a leg drainage bag that is about 300 mL to about 700 mL may be used. In other instances, a night drainage bag that is about 1 to 2 L may be used. However, any size bag may be used. The container may be made of any suitable material. Preferably, the container is a flexible plastic or rubber water-tight material. The container may be anti-microbial. While the collector was described with having an air vent, such as an air hole or an air valve, an air vent could also be present in the drainage container. That is, the air vent could be present in the drainage container 200 in addition to, or in lieu of, the vent on the collector 100. However, when the air vent is present in the drainage container, it is preferably an air permeable, liquid impermeable vent, as it is more likely to be in contact with liquids.

The drainage container 200 may include a connection member 240 at one end that is configured to be coupled to the collector 100. For example, an interference fit or fastener may be used to couple the collector 100 to the drainage container 200. As shown in FIG. 2, the connection member is a screw-top type closure device. Female threads may be at the opening of the drainage container 200 to serve as the connection member 240. However, in some embodiments, male threads serve as the connection member of the drainage container and female threads serve as the connection member of the collector. For example, male threads may be present at the end of the distal portion 120 and the male threads may be configured to couple to female threads at the opening of the drainage container. That is, male or female threads at the distal portion 120 of the collector may be configured to be coupled to male or female threads at the drainage container, or may be configured to be coupled to male or female threads at tubing, which is then configured to be coupled to the drainage container. If tubing is used, it can be any suitable tubing for use in urine catheters. Generally, urinary catheter tubing is flexible and compatible with urine. The tubing could be built onto the opening of the drainage bag (i.e., integral with the opening of the drainage bag), built onto the outlet of the collector (i.e., integral with the outlet of the collector), or a separate piece having any suitable length. When a separate length is used, it can include an interference fit or fastener (such as the above described screw-top fastener) to mate with the collector and the drainage container.

Generally, backflow is prevented by keeping the drainage container 200 below the user's penis. It is important to prevent backflow of urine, as urine backflow could lead to infections. In some embodiments, a backflow preventer 242 may be included at the connection member 240 to prevent urine from moving from the drainage container 200 up to the collector 100. The backflow preventer may be of any suitable design as long as it substantially prevents the flow of urine from the drainage container 200 back up to the collector 100. As depicted in FIG. 2, the backflow preventer 242 may seal the connection member 240. In this embodiment, once urine enters the drainage container, it cannot reenter (or is substantially prevented from reentering) the drainage container inlet because of the backflow preventer 242. In some embodiments, the backflow preventer may be a check valve. While the backflow preventer is described as being part of the drainage container, the backflow preventer could be at any suitable portion of the system, and could be affixed to the connection member of the distal portion of the collector or the tubing between the collector and the container. However, any type of backflow preventer may be used, and furthermore, such a backflow preventer may be present at any suitable position in the system.

The drainage container 200 may also include a drainage valve 244 at the opposite end of the connection member 240. The drainage valve 244 allows urine to be drained from the drainage container 200. The valve may be any suitable valve commonly used in urinary drainage bags. The valve is preferably relatively easy to operate so that a user may empty the drainage container 200 when necessary without assistance.

The drainage container 200 may include tie holes 246. One tie hole may be provided at each corner. Straps may be fixed to each tie hole so that a user can secure the container to his leg. In some embodiments, straps snap on to the container, while in other embodiments, straps are integrated into the container. However, any suitable method for affixing the container to a user may be used.

FIG. 3A depicts a catheter system 300 according to embodiments of the present invention in position on a user's body. The catheter system 300 includes an external collector 310 fixed to a drainage container 320. A retaining structure 330 urges the external collector 310 against a user's body.

In FIG. 3A, the retaining structure 330 is depicted as a pair of briefs. The retaining structure 330 can be any type of garment or undergarment, such as boxer shorts, briefs, jock straps, etc. The undergarment should be made so that it can hold the collector against the user's body with sufficient pressure. For instance, the fabric and elastic may be selected so that it is tear-resistant and has sufficient strength to hold the collector against the user. Suitable fabrics include denim or reinforced canvas, however, any suitable fabrics may be used.

If an undergarment is the retaining structure, the undergarment should include at least one opening or hole 332 in the front and middle to accommodate the collector. The front middle of the undergarment may be reinforced for strength. In some embodiments, the hole is circular, while in other embodiments, the hole is a square, or any other suitable shape. The hole has a diameter or opening that is greater than the diameter or cross sectional width of the second portion of the collector, but smaller than the diameter or cross sectional width of the first portion of the collector. Accordingly, the end of the distal portion of the collector, including the connection member 126, is able to extend through the hole 332, while the other parts of the collector cannot extend through the hole 332. Thereby, the retaining structure urges the collector against the user's body. In some embodiments, multiple holes are present in the underwear, as shown in FIG. 3. This allows a user to adjust the position of the collector 310 to adjust the amount of pressure of the collector against the user's body. Increasing the pressure may aid in substantially preventing the flow of urine, while excess pressure may be uncomfortable. Accordingly, the collector may be moved to a different hole 332 depending on the amount of pressure needed.

Figures 3B, 4:
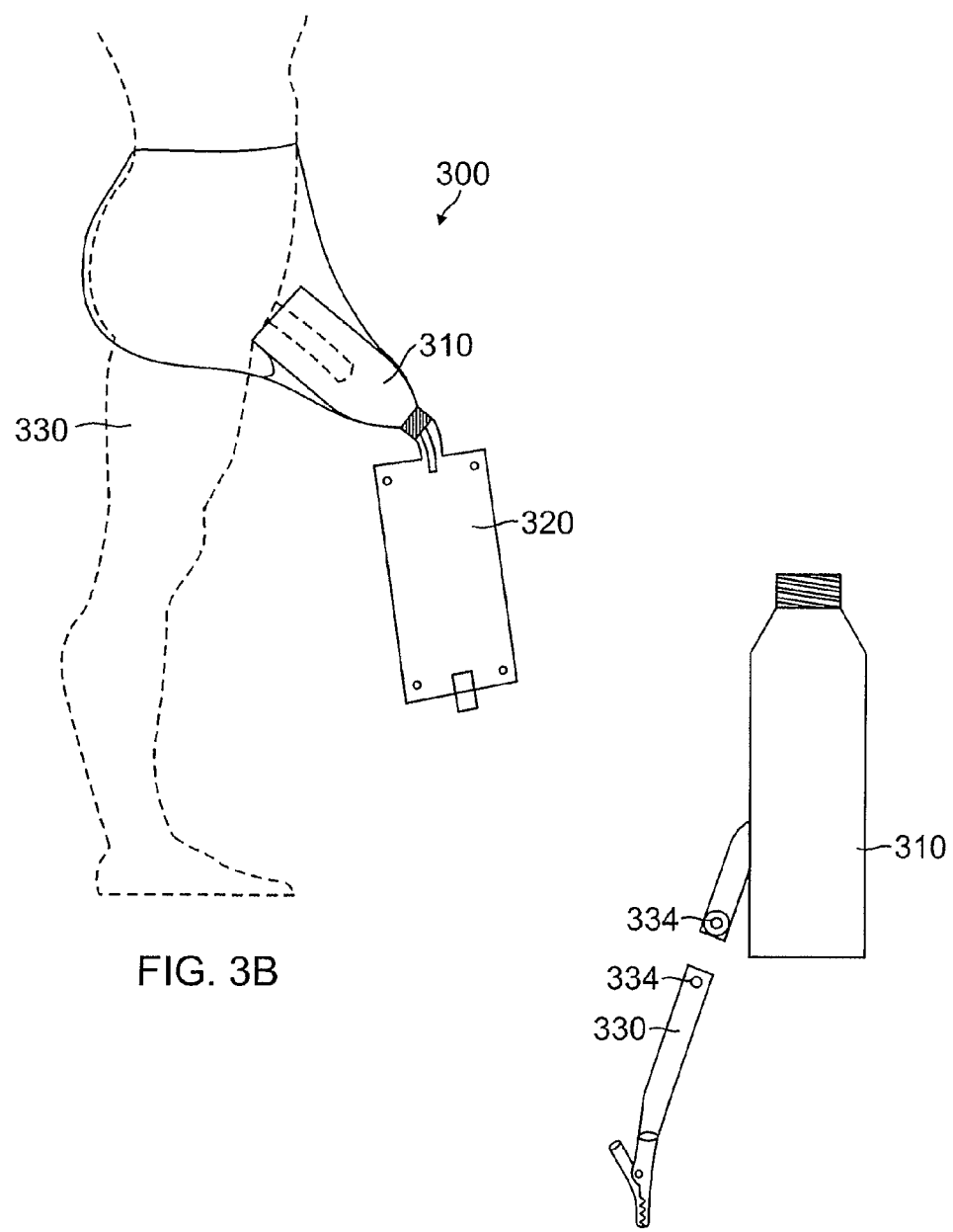
FIG. 3B is a cross-sectional view of an external urinary catheter system of FIG. 3.
FIG. 4 is a retaining structure for an external urinary collector according to an embodiment of the invention.

FIG. 4 depicts an alternative retaining structure. In FIG. 4, the retaining structure is one or more straps 330 or other retainers affixed to the external collector 310. The strap is used to urge the external collector 310 against the user's body to impede the flow of urine, as described above. In some embodiments, the strap wraps around the user's waist, thereby holding the collector against the user. In other embodiments, a single strap is affixed to the user's clothing to hold the collector against the user. The strap may be affixed to the external collector using fasteners, e.g., snaps 334 or buttons. A portion of the snap or other fastener may be built in to the collector. A single strap may be used, or two ore more straps may be used. In some embodiments, the strap may have a fastener to fix the strap to the user's clothing. For example, the strap fastener may be an alligator clip 336 that may be clipped onto a user's shirt or underwear to hold the collector in place. The strap may be made of any suitable material. For example, the strap may be a fabric, a fabric containing an elastic material, a rubber, polymer or other flexible material, or any other suitable material. The material of the strap should have sufficient strength to urge the collector against the user's body.

In an embodiment, to use the system, the collector is placed over the user's penis as shown in FIG. 3A. Then, when undergarment 330 is the retaining structure, part of the distal portion of the collector 310 is placed through an opening in the retaining structure to hold the collector 310 to the user and to urge the collector 310 against the user. Alternatively, when a strap is used as the retaining structure, it may be affixed to the collector and wrapped around the user to hold the collector to the user and to urge the collector against the user or clipped to the user's clothing to urge the collector against the user. The connection member of the drainage container 320 is then screwed onto the connection member of the collector (or are otherwise fixed to one another using another suitable connection). While not bound by any theory, it is believed that as a result of the pressure of the collector against the user's urethra, the user's flow of urine is substantially stopped when the user is laying down or sitting. However, when the user stands, pressure against the user is lessened, and the user's flow of urine may resume.

Figure 5:
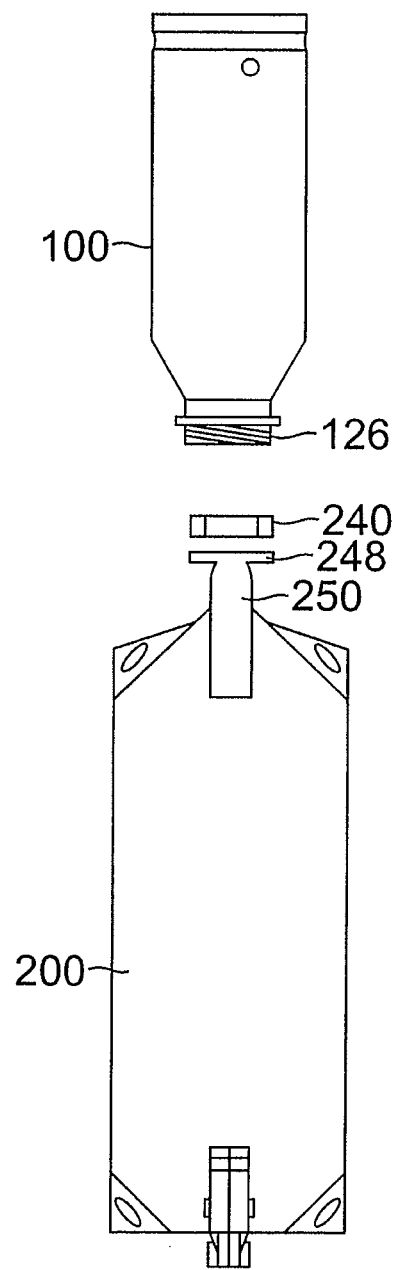
FIG. 5 is a schematic view of an external urinary collector and drainage container according to an embodiment of the invention.

Another embodiment of the invention is depicted in FIG. 5. The collector 100 and container 200 are similar to the embodiments depicted in FIGS. 1 and 2 except for the connection members. The collector includes a connection member 126 at the end of the distal portion. The connection member 126 is a screw-top type fastener. For example, the connection member 126 may include male threads. The lid 240 includes female threads configured to mate with the male threads of the connection member 126. The lid is also substantially open on both ends, except that on the top it has a lip that extends toward the center of the lid. A flange 248 is attached to tubing 250 that is affixed to the end of the container 200. The tubing 250 may be any suitable length, e.g., 1-12 inches (such as 6 inches), and may be integrated with the container, by, e.g., integrally forming the tubing and the container or melting the two parts together. The flange 248 may be made of a flexible rubber or other gasket-type material. The flange 248 may be flexible so that it can be inserted into the top of the lid and seated in the lip. In order to use the device, the flange 248 may be seated in the lip of the lid 240, and the lid may then be mated with the connection member 126, as in the lid of a baby bottle. Such a connection has a relatively tight seal and may aid in preventing leakage. While some embodiments of the connection of the collector to the container have been described, any suitable connection may be used. The two components may be directly connected, or tubing may be between the two components, or tubing may be fixed to one of the components and the tubing may be fixed to the other component.

Figure 6A:
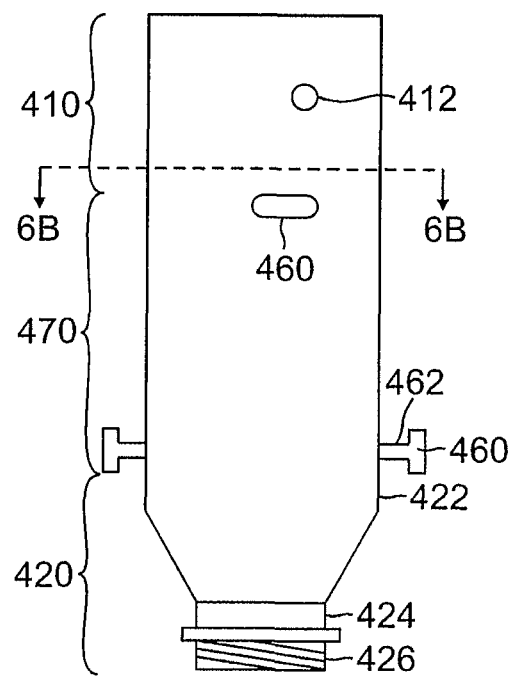
FIG. 6A is a schematic view of an external urinary collector according to an embodiment of the invention.
Figure 6B:
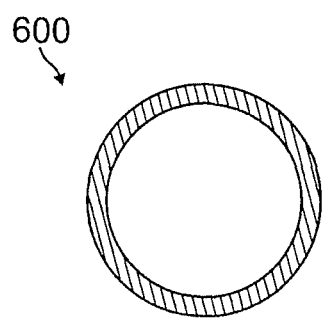
FIG. 6B is a cross-sectional view of the external urinary collector of FIG. 6A.

FIGS. 6A and 6B depict another embodiment of the present invention. As the external urinary collector 600 of FIGS. 6A and 6B is similar to that of FIGS. 1A and 1B, like parts may not be described in detail. As shown in FIG. 6A, an external urinary collector 600 includes a proximal portion 410, an intermediate portion 470, and a distal portion 420. The collector 600 includes an air vent 412 and the distal portion 420 includes a first portion 422 and a second portion 424. As shown in FIG. 6A, a pressure pad and a groove may be omitted, and as shown in FIG. 6B, an internal cushion and external cushion may be omitted.

The proximal and intermediate portions 410, 470 may be formed of a softer, more pliable plastic, plastic-like, or polymeric material. Preferably, this material is bacteria resistant and easily cleaned. However, as stated above, the collector is a self-supporting structure (substantially semi-rigid or rigid) so that a force applied to the distal portion (or, e.g., at the buttons 460) is transmitted to the proximal portion 410. By using a soft material, the collector may not irritate the user's penis and/or testicles, or at least, the soft material may reduce the amount of irritation, and furthermore, no pressure pad at the proximal end of the collector may be needed. Alternatively, the softer material may be coated onto, fabricated with, blended into, or otherwise joined to an internal rigid plastic, plastic-like, or polymeric material. As the distal portion 420 is not designed to be in contact with the user's penis or testicles, it may be made of a harder plastic material, like that discussed above. The distal portion may then be joined to the intermediate portion, the distal portion may be fabricated along with the intermediate portion and proximal portion, and/or the intermediate portion including the softer, more pliable material may be blended into the distal portion. As shown in FIG. 6B, when the proximal and intermediate portions include a softer, more pliable material, no additional internal or external cushions may be necessary.

The collector 400 may also include buttons 460 (e.g., strap buttons or a button raised on a post 462). The buttons 460 may be integrally formed with the collector, or alternatively, may be blended into or otherwise joined to the collector 400. The post 462 may be circular or any suitable shape, while the button may be circular, elliptical, or any other suitable shape. When the button is elliptical, a strap may be securely fastened to the button. For example, a rubber or polymer type strap may include a slit near one end and the slit may be stretched to fit over the button 460 to securely fix the strap to the button 460. As shown in FIG. 6A, the collector may include three buttons. However, any suitable number of buttons may be used. Furthermore, while one button is shown near the proximal portion and two buttons are shown near the distal portion on the sides, the buttons can be located in any suitable position. When the buttons are used, as stated above with respect to FIG. 4, the retaining structure may be one or more straps or other retainers affixed to the collector 400. The straps may be fixed to the buttons and then used to urge the external collector against the user's body to impede the flow of urine, as described above. In some embodiments, a strap may wrap around the user's waist, thereby holding the collector against the user. In other embodiments, a single strap is affixed to the user's clothing to hold the collector against the user. A single strap may be used, or two or more straps may be used. In some embodiments, the strap may have a fastener to fix the strap to the user's clothing. In some embodiments, one strap may be configured to wrap around a user's body and be affixed to two buttons, and another strap may be configured to be affixed to the user's clothing and be affixed to one button. However, any number of buttons and any suitable positions for the buttons may be used.

Although the present invention has been described and illustrated in respect to exemplary embodiments, it is to be understood that it is not to be so limited, since changes and modifications may be made therein which are within the full intended scope of this invention as hereinafter claimed.

What is claimed is:

1. A male external urinary catheter system comprising:
   an external collector having a proximal end configured to receive a user's penis and a distal end opposite the proximal end, the external collector defining a longitudinal axis,
   a retaining structure configured to engage the distal end of the external collector to urge the proximal end of the external collector against the user's body adjacent the base of the penis to provide sufficient pressure to the user's body adjacent the base of the penis to impede urinary drainage from the user's penis while the user is sitting or laying, and
   a drainage container coupled to the distal end of the external collector,
   wherein the retaining structure comprises a garment having at least one opening in the front, the at least one opening having an opening diameter,
   wherein the distal end of the external collector comprises a first portion having a first diameter and a second portion at the end of the distal portion having a second diameter that is smaller than the first diameter, the second diameter being smaller than the opening diameter and the first diameter being larger than the opening diameter,
   wherein the distal end of the external collector is configured to extend through the at least one opening in the garment,
   wherein the external collector is straight along the longitudinal axis from the proximal end to the distal end, and
   wherein the external collector is rigid from the proximal end to the distal end.

2. The male external urinary catheter system of claim 1, wherein the distal end of the external collector comprises threads configured to mate with a threaded opening of the drainage container.

3. The male external urinary catheter system of claim 1, wherein the distal end of the external collector comprises threads configured to mate with tubing that is coupled to the drainage container.

4. The male external urinary catheter system of claim 1, wherein the drainage container is a leg bag.

5. The male external urinary catheter system of claim 1, wherein the drainage container comprises a backflow prevention device at an opening of the drainage container.

6. The male external urinary catheter system of claim 1, wherein the external collector is cylindrical.

7. The male external urinary catheter system of claim 1, wherein the external collector comprises an air vent proximate the proximal end.

8. The male external urinary catheter system of claim 1, wherein the external collector comprises a circumferential groove proximate the proximal end.

9. The male external urinary catheter system of claim 1, wherein an internal cushion is disposed inside the external collector.

10. The male external urinary catheter system of claim 1, wherein an external cushion is disposed on an external surface of the external collector.

* * * * *